United States Patent [19]

Lehmann et al.

[11] Patent Number: 5,730,999
[45] Date of Patent: Mar. 24, 1998

[54] DERMAL THERAPEUTIC SYSTEM MADE OF A MELTABLE POLY (METH) ACRYLATE

[75] Inventors: Klaus Lehmann, Rossdorf; Hans-Ulrich Petereit, Darmstadt; Manfred Assmus, Bickenbach, all of Germany

[73] Assignee: Roehm GmbH Chemische Fabrik, Darmstadt, Germany

[21] Appl. No.: 650,025

[22] Filed: May 17, 1996

Related U.S. Application Data

[63] Continuation of Ser. No. 217,850, Mar. 25, 1994, abandoned.

[30] Foreign Application Priority Data

Mar. 27, 1993 [DE] Germany ............ 43 10 012.0

[51] Int. Cl.$^6$ ................... A61K 9/70
[52] U.S. Cl. ................... 424/443; 424/449
[58] Field of Search ............ 264/173.16, 174.1; 424/443, 449

[56] References Cited

U.S. PATENT DOCUMENTS

| | | | |
|---|---|---|---|
| 3,557,265 | 1/1971 | Chisholm et al. | 264/173.16 |
| 3,577,512 | 5/1971 | Shepherd et al. | 424/482 |
| 4,162,165 | 7/1979 | Schwab | 428/307 |
| 4,235,458 | 11/1980 | Austin et al. | 427/151 |
| 4,540,623 | 9/1985 | Im et al. | 264/174.1 |
| 4,606,909 | 8/1986 | Bechgaard et al. | 124/482 |
| 4,826,677 | 5/1989 | Mueller et al. | |
| 4,997,643 | 3/1991 | Partain, III et al. | |
| 5,286,493 | 2/1994 | Oshlack et al. | 424/482 |
| 5,462,708 | 10/1995 | Swenson et al. | 264/174.11 |

FOREIGN PATENT DOCUMENTS

| | | |
|---|---|---|
| 0 315 218 | 5/1989 | European Pat. Off. . |
| 0 394 956 | 10/1990 | European Pat. Off. . |
| 415 055 | 3/1991 | European Pat. Off. . |
| 32 08 853 | 9/1982 | Germany . |
| 856 501 | 12/1960 | United Kingdom . |
| 1 462 356 | 1/1977 | United Kingdom . |

OTHER PUBLICATIONS

Research Disclosure 17619 (Anonymous) Derwent WPI Acc No. 78-92367 A/51.

Research Disclosure 17620 (Anonymous) Derwent WPI Acc No. 78-92368A/51.

*Primary Examiner*—Peier F. Kulkosky
*Attorney, Agent, or Firm*—Oblon, Spivak, McClelland, Maier & Neustadt, P.C.

[57] ABSTRACT

A dermal therapeutic system which exhibits a prolonged release of a drug comprising at least one pharmaceutical agent combined with poly(meth)acrylates in the form of at least one layer of the therapeutic system, the poly(meth) acrylates being a mixture, which is produced from a melt, comprising (1) at least one (meth)acrylic polymer containing functional groups and (2) at least one (meth)acrylic polymer which regulates the flow behavior of the poly(meth)acrylate mixture and which contains no functional groups or only insignificant amounts of functional groups.

10 Claims, No Drawings

DERMAL THERAPEUTIC SYSTEM MADE OF A MELTABLE POLY (METH) ACRYLATE

This application is a Continuation of application Ser. No. 08/217,850, filed on Mar. 25, 1994, now abandoned.

BACKGROUND OF THE INVENTION

1. Field of the Invention

The present invention relates to therapeutic systems having dermal or transdermal action and are intended for application to the skin, in which the delivery of the active substance to the skin is controlled by polymers.

2. Discussion of the Background

A controlled and continuous release of drugs to the skin or through the skin is usually achieved with the use of patches in which an adhesive mass is formulated together with a pharmaceutical layer and a carrier foil or fabric web in a laminate preparation.

The adhesives used for attaching superficial, flexible substrates to the skin are pressure-sensitive dermal contact adhesives. Dermal contact adhesives are not only able to firmly and permanently-elastically attach drug-containing substrates, such as wound plasters or medicinal adhesive patches, to the skin. They are also suitable for creating drug-containing, locally or transdermally active layers adhering to the skin, i.e. pharmaceuticals with a topical or systemic pharmaceutical agent. An advantageous aspect of this type of pharmaceutical is its function as a depot preparation for the delayed release of drug and thus provides for longer action of the drug.

In general, such dermal or transdermal systems are constituted of several layers which include a carrier foil, a depot layer with a pharmaceutical, diffusion-controlling layer, a skin-adhesive layer, and a cover foil which is removed prior to use. In order to simplify manufacturing, there is frequently a desire to employ less layers and to combine the function of several layers in one layer, which in the simplest case, is only one layer which adheres to the skin and which also contains the drug. Carrier foil and cover foil then fulfill only packaging functions.

Dermal contact adhesives are manufactured from tacky polymers of natural or synthetic origin. Synthetic polymers which can be fixed to the skin and which have been known for many years as skin contact adhesives and which have been used for transdermal therapeutical systems are film-forming poly(meth)acrylates which, because of their manufacturing, offer a wide variety of possible properties.

DE-OS 36 12 305 describes a pharmaceutical agent for the localized and low-irritation therapy of psoriasis. The agent consists of known anti-psoriatic agents and of film-forming polymers in solution or dispersion, from which the therapeutically active film forms after application onto the affected skin location.

EP-A 0 394 956 introduces anionic (meth)acrylate copolymers, and EP-A 0 415 055 cationic (meth)acrylate copolymers, which, in the form of their water-dissolved salts, are equally suited for forming dermal contact adhesives for wound plasters and for forming a transdermally active pharmaceutical intended for application to the skin.

German patent DE-C 32 08 853 claims a pharmaceutical compound preparation for adhesion to the skin by way of a self-adhesive mass which also contains the pharmaceutical agent in a higher concentration than corresponds to its solubility in the adhesive substance, wherein this mixture is applied to a polymer film through which the drug is able to migrate. Here, the requirements regarding adhesion properties, compatibility, solubility, and releasability are best fulfilled by acrylic copolymers. Acrylic copolymers are preferably acrylic copolymers which contain at least 50% by weight alkyl acrylate or alkyl methacrylate with an average of at least 4 carbon atoms in the alkyl residue. They are formulated as a transdermal therapeutic system in the form of a solution with the drug.

Because of their good skin compatibility, poly(meth)acrylates are excellent additives for dermal pharmaceuticals. However, because of flammability and toxicity of the solvents, the application of such polymers in the form of organic solutions is associated with extensive technical and organizational expenditure for the protection of operating personnel and for disposal of the solvents. Aqueous dispersions can be handled without danger, but their drying requires high energy expenditure, carefully controlled drying procedures, and thus also complicated technical installations. The dispersions which can be used are also susceptible to microbiological growth, exhibit limited storage stability, may coagulate when the drug is added, and contain emulsifiers which may have a significant adverse effect on the function of the pharmaceutical form and its stability in storage, as well as on its skin compatibility.

SUMMARY OF THE INVENTION

Accordingly, one object of the present invention is to provide a dermal therapeutic system of simplified construction which readily adheres to the skin thereby providing for the prolonged release of a therapeutic agent.

Briefly, this object and other objects of the present invention as hereinafter will become more readily apparent can be attained by a dermal therapeutic system which comprises at least one pharmaceutical agent combined with poly(meth)acrylates in the form of at least one layer of said therapeutic system, said poly(meth)acrylates being a mixture, which is produced from a melt, comprising (1) at least one (meth)acrylic polymer containing functional groups and (2) at least one (meth)acrylic polymer which regulates the flow behavior of the poly(meth)acrylate mixture and which contains no functional groups or only insignificant amounts of functional groups.

DETAILED DESCRIPTION OF THE PREFERRED EMBODIMENTS

It has now been found that pharmaceuticals for dermal or mucous membrane release can be easily formulated by melting and spreading (hot-melt process) of selected mixtures of poly(meth)acrylates. By adapting the polymer components such that the resulting polymer combination accepts drugs and other additives such as softeners, penetration-promoting substances, and the like, it is now possible to control the release of drug to the skin and to achieve therapy-specific release profiles.

The polymer components to be mixed are selected according to the following two important factors:

1. The influence on drug release through (meth)acrylic polymers containing functional groups.

2. The influence on the melt and flow behavior of the product blend by poly(meth)acrylates which contain no or only insignificant amounts of functional groups. Additional softeners are possibly needed to reduce the melting temperature and melting viscosity.

The present dermal therapeutic laminate system, which exhibits delayed drug release characteristics, contains at least one pharmaceutical agent, and is constituted of one or more layers which are composed of mixtures of poly(meth) acrylates that are produced from a melt, with a given mixture consisting of polymer component (1), which is one or more (meth)acrylic polymers containing functional groups, and polymer component (2) which regulates the flow behavior of the product blend and which contains at most only insignificant amounts of functional groups.

Usually, the polymer components are combined in weight ratio of polymer component (1) to polymer component (2) of between 20:1 and 1:20. The relative amounts chosen generally depend on the release properties of the pharmaceutical agent and on the flow behavior of the product blend.

The polymeric components which are mixed are such that one type is a (meth)acrylate polymer which contains functional groups and which is able to influence drug release through interaction with the system, while the other type is a (meth)acrylate polymer which consists essentially of $C_1$- to $C_{12}$-alkyl esters of (meth)acrylic acid, with no more than insignificant amounts of monomers having functional groups and which regulate the melt and flow behavior of the adhesive polymer adhesive product.

The molecular weights of the polymers used in the present invention range between 10,000 and 2,000,000 g/mol.

In order to reduce the melting temperature and melting viscosity of the polymer mixture, it is possible to also add softeners with a low molecular weight.

Pharmaceutical additives, such as penetration-promoting or -inhibiting substances, preservatives, dyes, and the like also can be added.

(i) The drug-containing dermal contact adhesives of the present invention are manufactured by using acrylic resins as poly(meth)acrylates which contain functional groups, e.g. acrylic resins which are known e.g. for the coating of pharmaceuticals under the name ®Eudragit. These polymers are copolymers of methacrylic esters and acrylic esters and possibly other vinyl monomers, with monomers with functional groups, which causes the polymers to have cationic, anionic or hydrophilic character. The functional polymer should be composed so that the film formed from it is dry and hard, yet not brittle. This spectrum of properties is exhibited by polymer films with a dynamic glass temperature (also known as $T_{max}$ of $T_{g(dym)}$) according to DIN 53445 which ranges from $-10°$ to $100°$ C., preferably $10°$ to $60°$ C. Comonomers contributing the functional character of the (meth)acrylate polymers are e.g. acrylic acid, methacrylic acid, maleic acid for anionic polymers, or N-dimethylaminoethylmethacrylate or -acrylate, N-[3-(dimethylamino)-2,2-dimethylpropyl]-methacrylamide for cationic polymers, or 2-hydroxyethyl(meth)acrylate, 2-hydroxypropyl(meth) acrylate, and trimethylammoniumethyl(meth)acrylate chloride for polymers with a hydrophilic character.

The functional poly(meth) acrylates used according to the invention are prepared in the usual known manner by substance polymerization, solution polymerization or emulsion (dispersion) polymerization. To prepare the polymer mixtures, the polymer is used as a solid in the form of a granulate or powder with particle sizes of approximately 0.1 to 0.5 mm, for which purpose it is obtained after polymerization, e.g. by granulating of extruded substance polymer, such as e.g. cationic copolymers; or by spray drying or freeze drying of emulsion polymers with particle sizes of approximately 50 to 500 μm, such as e.g. acid group-containing, anionic poly(meth)acrylates; or by evaporation or precipitation of polymer solutions.

Examples of poly(meth)acrylates with functional groups include:

Copolymer with approximately 50 wt. % monomer units with tertiary amino groups: ®Eudragit E 100.

Copolymer with approximately 10 wt. % quaternary ammonium groups: ®Eudragit RS 100.

Copolymer with approximately 50 wt. % monomer units with carboxylic acid groups: ®Eudragit L 100-55 or ®Eudragit L 100.

Copolymer with approximately 30 wt. % monomer units with carboxylic acid groups: ®Eudragit S 100.

Copolymers with approximately 70 wt. % monomer units with carboxylic acid groups: ®EUDISPERT.

Copolymers of methacrylate and butylacrylate with more than 10 wt. % methacrylic acid.

Copolymers with hydroxyalkyl (meth)acrylate.

(ii) Polymers without or with only insignificant amounts of functional groups which in the mixture according to the invention affect the melt and flow behavior, as well as the stickiness of the new dermal and transdermal therapeutical systems, are poly(meth)acrylates whose dynamic glass temperatures according to DIN 53445 range from $-70°$ to approximately $80°$ C. Particularly preferred are poly(meth) acrylates whose glass temperatures range from $-50°$ to $+70°$ C., primarily from $+10°$ to $70°$ C.

Examples of such polymers include:

Copolymers of ethyl acrylate and methyl methacrylate, preferably with more than 30 wt. % ethyl acrylate.

Copolymers of ethyl acrylate and methyl methacrylate with ca. 5% trimethylammonioethyl methacrylate chloride.

Copolymers of methyl acrylate and methyl methacrylate.

Copolymers of methyl methacrylate with butyl (meth) acrylate and/or 2-ethylhexyl methacrylate.

(iii) Dermal and transdermal agents, whose release from the therapy system applied to the skin is controlled by the polymer combination of (1) and (2), must be capable, because of their physicochemical properties, to build up a therapeutically effective concentration at the site of action. Dermal therapy frequently requires the penetration of drug molecules into deeper skin layers. Systemic effects require the complete passage through the skin, particularly through the stratum corneum, so that the drug, after being absorbed into the blood stream, is distributed in the body. For processing according to the invention, the drugs should have a sufficient thermal stability at a minimum temperature of $50°$ C. Examples are known e.g. from DE-C 3 208 853 and from extensive literature, and include:

(I) Corticosteroids, e.g. hydrocortisone, prednisolone, betamethasone.

(II) Analgetic, anti-inflammatory agents, e.g. ibuprofen, ketoprofen, fentanyl.

(III) Antihypertensive agents, e.g. clonidine and kallikrein.

(IV) Antibiotics, e.g. chloramphenicol, neomycin.

(V) Anesthetics, e.g. lidocaine.

(VI) Fungicides, e.g. clotrimazole.

(VII) Vitamins and derivatives, e.g. vitamin A acid, cholecalciferol.

(VIII) Anti-epileptics, e.g. nitrazepam.

(IX) Coronary vasodilators, e.g. nitroglycerine, isosorbide dinitrate.

(X) Antihistamines, e.g. diphenhydramine hydrochloride.

(XI) Antipsoriatic agents, e.g. dithranol.

(XII) Other agents, such as nicotine.

(XIII) Hormones, e.g. estradiol, testosterone.

(XIV) Antiemetics, e.g. scopolamine salts.

The therapy system may contain single agents or a combination of agents. Their amount in the system accounts for 0.2 to 50 wt. %, preferably 0.5 to 20 wt. % related to the polymer mixture.

(iv) If necessary, the mixtures of components (i), (ii), and (iii) may contain further additives, e.g. softeners, penetration-promoting substances such as e.g. laurocapram, DMSO, or DMF, keratolytic substances, such as e.g. salicylic acid, urea, or fillers in the form of fine powder, e.g. of $SiO_2$ or $CaCO_3$.

The carrier foils may have a thickness of preferably 50 to 500 μm. They are composed of common polymers such as PP, PE, PVC, polyesters, polyurethane, or polymethacrylates, or of aluminum. The mechanical stability should enable both uncomplicated coating and also sufficient flexibility when worn on the skin. The foils are frequently dyed in skin color. If necessary, the carrier foils themselves may already be constructed in layers, e.g. polymer/aluminum combinations in order to prevent the penetration of the agent into the carrier, or primer coatings in order to improve the adhesion of the drug/polymer matrix on the carrier.

Peeling foils which are removed prior to application consist principally of the same materials.

Adhesion-reducing coatings, such as e.g. silicone compounds, promote removal by simply peeling the coating from an area to which it is applied.

The essentially powdered components (i), (ii), (iii), and potentially (iv), are mixed well in a kneader with slight pressure and are heated to temperatures ranging from 50° to 200° C., particularly from 80° to 120° C., and the molten mass is spread onto a carrier foil, whereby the thickness of the drug-containing polymer layer is set from 10 to 600 μm, particularly from 50 to 300 μm. The carriers which are used are the usual superficial substrates such as foils of plastic or metal, particularly aluminum, textiles, or papers.

The therapeutic system with poly(meth)acrylates having functional groups which is manufactured according to the present invention enables a controlled release of the drug to the skin, and in the case of drugs which penetrate through the skin, also their absorption by the skin. The combination with poly(meth)acrylates having a low glass temperature enables the simple manufacture of meltable therapeutic formulations which also have the properties of a pressure-sensitive dermal contact adhesive.

Having generally described this invention, a further understanding can be obtained by reference to certain specific examples which are provided herein for purposes of illustration only and are not intended to be limiting unless otherwise specified.

EXAMPLE 1

A premix of drug and polymer is prepared by stirring 100 mg of prednisolone suspended in 5 ml of water, 5 g of polymer powder made from equal weight parts of methacrylic acid and ethyl acrylate, and 5 ml of a 30% aqueous polymer dispersion made from ethyl acrylate and methyl methacrylate at a weight ratio of 7:3. The premix is dried to a film at 40° C. and melted at 140° C. This results in a soft, kneadable mass. The drug is released over time in vitro from a delivery system according to USP (=United States Pharmacopeia USP XXII 1990, p. 1581, Transdermal Delivery Systems, General Drug Release Standards, Apparatus 3 Paddle over disk.) from a film piece measuring 4×4 cm and 0.6 mm thick containing approximately 32 mg of prednisolone in contact with a phosphate buffer at pH 6.8 as follows:

| after hours | % of drug released: |
|---|---|
| 1 h | 13% |
| 2 h | 20% |
| 3 h | 28% |
| 23 h | 62% |
| 28 h | 74% |

EXAMPLE 2

A premix is prepared by stirring 100 mg of prednisolone suspended in 3 ml of water, 5 ml of a 30% aqueous polymer dispersion made from ethyl acrylate and methyl methacrylate at a weight ratio of 7:3, and 5 ml of a 30% polymer dispersion made from methacrylic acid and methacrylate at a weight ratio of 8:2. The premix is dried at 40° C. and melted at 120° C. The following release of the drug from a film piece measuring 4×4 cm and 0.3 mm thick is determined according to the USP method described in Example 1:

| after hours | % of drug released: |
|---|---|
| 1 h | 25% |
| 2 h | 38% |
| 3 h | 45% |
| 5 h | 55% |
| 24 h | 66% |
| 48 h | 72% |

EXAMPLE 3

The procedure of Example 2 is repeated except that the polymer dispersion made from methacrylic acid and methacrylate has a weight ratio of these monomers of 9:1. The prednisolone is released clearly faster, i.e. as follows:

| after hours | % of drug released |
|---|---|
| 1 h | 11% |
| 2 h | 20% |
| 3 h | 25% |
| 5 h | 35% |
| 24 h | 58% |
| 48 h | 71% |

EXAMPLE 4

The procedure of Example 2, is repeated except that 100 mg of ketoprofen is employed instead of prednisolone as the drug. The drug is released in vitro according to USP as described in Example 1 as follows:

| after hours | mg of drug released |
|---|---|
| 1 h | 8.3 mg |
| 2 h | 9.9 mg |
| 4 h | 10.9 mg |
| 24 h | 11.2 mg |
| 48 h | 11.8 mg |

EXMAPLE 5

The procedure of Example 3, is repeated except that 100 mg of ketoprofen is employed instead of prednisolone. The drug is released in vitro according to USP as described in (Example 1) as follows:

| after hours | mg of drug released |
| --- | --- |
| 1 h | 3.5 mg |
| 2 h | 5.4 mg |
| 4 h | 9.0 mg |
| 24 h | 14.4 mg |
| 48 h | 17.0 mg |

EXAMPLE 6

A 196 g amount of ®EUDRAGIT E 100 and 196 g of ®PLASTOID B are heated with 156 g of triethyl citrate in a kneader to approximately 120° C. and are mixed uniformly. This results in a clear, low viscosity mass. 50 g of ketoprofen are added to 450 g of this polymer mixture and are distributed uniformly.

This melt is then distributed on a 50 µm thick aluminum foil so as to form 1.9 mm thick layers and is cooled until it solidifies.

Punching results in round patches with a diameter of approximately 4.4 cm and approximately 285 mg ketoprofen per single dose. The in vitro release is determined according to USP XXII, p. 1582, method 4 (cylinder) in phosphate buffer at pH 6.8 and yields the following values (related to initial drug loading):

| 1 h: | 13.0% |
| --- | --- |
| 3 h: | 24.5% |
| 6 h: | 41.0% |
| 12 h: | 59.8% |
| 18 h: | 91.1% |
| 24 h: | 96.8% |

EXAMPLE 7

A 166.6 g amount of ®EUDRAGIT E 100 and 166.6 g of ®EUDRAGIT RS 100 are mixed uniformly with 133.3 g of triethyl citrate in a heatable kneader at approximately 120° C. 50 g of ketoprofen are distributed uniformly in 450 g of the obtained clear, low viscosity melt, and the mass is spread onto aluminum foils at a thickness of approximately 50 µm in order to form layers with a thickness of 1.9 mm.

After solidifying, round patches with a diameter of 4.4 cm are punched out. Each single dose contains 285 mg of ketoprofen. The drug release is determined in vitro according to USP XXII, p. 1582, method 4 (cylinder) in phosphate buffer at pH 6.8 and yields the following values (related to the initial drug loading):

| 1 h: | 9.1% |
| --- | --- |
| 3 h: | 16.7% |
| 6 h: | 23.3% |
| 12 h: | 35.9% |
| 18 h: | 44.7% |
| 24 h: | 51.2% |

EXAMPLE 8

A ketoprofen/polymer mixture according to Example 7 is spread at approximately 120° C. with a hand spreader over aluminum foil (50 µm thickness) into 300 µm thick layers and is punched out after solidifying. Each individual dose contains 45 mg of ketoprofen.

Determination of the drug release according to Example 7 yields the following values:

| 1 h: | 31.3% |
| --- | --- |
| 3 h: | 66.6% |
| 6 h: | 78.3% |
| 12 h: | 88.6% |
| 18 h: | 90.3% |
| 24 h: | 91.0% |

EXAMPLE 9

A mixture of 166.6 g of EUDRAGIT L 100 and 166.6 g of ®EUDRAGIT RS 100 with 166.6 g of triethyl citrate is processed according to Example 7 and is analyzed. Determination of the drug release in vitro yields the following values:

| 1 h: | 2.9% |
| --- | --- |
| 3 h: | 5.7% |
| 6 h: | 10.3% |
| 12 h: | 18.4% |
| 18 h: | 22.8% |
| 24 h: | 29.4% |

EXAMPLE 10

The polymer/drug mixture according to Example 9 is processed along the lines of Example 8 and is analyzed, yielding the following results:

| 1 h: | 13.6% |
| --- | --- |
| 3 h: | 28.9% |
| 6 h: | 40.7% |
| 12 h: | 50.0% |
| 18 h: | 52.4% |
| 24 h: | 53.3% |

EXAMPLE 11

The drug release in ketoprofen patches according to Example 9 is analyzed at pH 5.5 in the apparatus described in Example 7. The results are as follows:

| 1 h: | 1.6% |
| --- | --- |
| 3 h: | 1.9% |
| 6 h: | 2.5% |
| 12 h: | 3.1% |
| 18 h: | 3.9% |
| 24 h: | 5.2% |

EXAMPLE 12

Ketoprofen patches according to Example 10 are analyzed according to Example 11 at pH 5.5. The drug release is faster:

| 1 h: | 7.1% |
| --- | --- |
| 3 h: | 9.6% |
| 6 h: | 12.5% |
| 12 h: | 16.1% |

| | |
|---|---|
| 18 h: | 19.1% |
| 24 h: | 21.8% |

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A dermal therapeutic system which exhibits a prolonged release of a drug, comprising:

at least one melt coated layer of at least one pharmaceutical agent and a mixture of poly(meth)acrylates comprising (1) at least one (meth)acrylic polymer containing functional groups having a glass transition temperature Tg of −10° to 100° C. and (2) at least one (meth)acrylic polymer having a glass transition temperature Tg ranging from −70° to 80° C. which regulates the melt flow behavior of the poly(meth)acrylate mixture and which contains no functional groups or only insignificant amounts of functional groups, wherein the weight amount of polymer component (1) to polymer component (2) ranges between 20:1 and 1:20 onto a support of a foil, textile or paper.

2. The dermal therapeutic system as claimed in claim 1, wherein said glass transition temperature of the poly(meth)acrylate (2) ranges from 10°–70° C.

3. The dermal therapeutic system as claimed in claim 1, wherein the poly(meth)acrylate containing functional groups is a cationic polymer with amino or ammonium groups.

4. The dermal therapeutic system as claimed in claim 1, wherein the poly(meth)acrylate containing functional groups is an anionic polymer with carboxy or carboxylate groups.

5. The dermal therapeutic system as claimed in claim 1, wherein the poly(meth)acrylate containing functional groups is a non-ionic polymer with alcoholic hydroxy groups.

6. The dermal therapeutic system as claimed in claim 1, wherein the at least one or more layers contain from 0.2 to 50 wt % of said at least one pharmaceutical agent.

7. The dermal therapeutic system as claimed in claim 1, wherein said pharmaceutical agent is a corticosteroid, an analgetic agent, an antihypertensive agent, an antibiotic, an anesthetic, a fungicide, vitamins, an anti-epileptic, a coronary vasodilator, an antihistamine, an antipsoriatic agent, hormones and antiemetics.

8. The dermal therapeutic system as claimed in claim 1, wherein the polymer/drug system contains low-molecular weight softeners.

9. A process for the manufacture of the dermal therapeutic system according to claim 1, comprising:

mixing at least one pharmaceutical agent with said poly (meth)acrylates, said mixed poly(meth)acrylates comprising said functional group containing (meth)acrylic polymer (1) and said non-functional group containing (meth)acrylic polymer (2) and optional excipients;

heating the mixture to melt the same; and spreading the molten material in a thin layer onto a support of a foil, textile or paper.

10. The process of claim 9, wherein the support is removable.

* * * * *

UNITED STATES PATENT AND TRADEMARK OFFICE
CERTIFICATE OF CORRECTION

PATENT NO. : 5,730,999
DATED : March 24, 1998
INVENTOR(S) : Klaus LEHMANN, et al.

It is certified that error appears in the above-identified patent and that said Letters Patent is hereby corrected as shown below:

On the title page, item [54] and on top of column 1, the last word of the title should be:

--MIXTURE--

Signed and Sealed this

Ninth Day of June, 1998

Attest:

BRUCE LEHMAN

Attesting Officer

Commissioner of Patents and Trademarks